(12) United States Patent
Mascarehas et al.

(10) Patent No.: US 6,476,297 B1
(45) Date of Patent: Nov. 5, 2002

(54) MEIOSIS PROMOTER

(75) Inventors: Joseph P. Mascarehas, Delmar, NY (US); Caiping He, Montreal (CA)

(73) Assignee: The Research Foundation of State University of NY, Albany, NY (US)

( * ) Notice: Subject to any disclaimer, the term of this patent is extended or adjusted under 35 U.S.C. 154(b) by 0 days.

(21) Appl. No.: 09/349,740

(22) Filed: Jul. 8, 1999

Related U.S. Application Data (60) Provisional application No. 60/092,277, filed on Jul. 10, 1998.

(51) Int. Cl.[7] .................. C12N 15/09; C12N 15/29; C12N 15/82; A01H 5/00
(52) U.S. Cl. .................. 800/303; 800/306; 800/278; 800/287; 800/298; 435/69.1; 435/320.1; 435/468; 435/419; 536/23.1; 536/24.1; 536/23.6
(58) Field of Search .................. 800/303, 306, 800/278, 287, 298; 536/23.1, 24.1, 23.6; 435/69.1, 320.1, 468, 419

(56) References Cited

U.S. PATENT DOCUMENTS

| | | | |
|---|---|---|---|
| 5,107,065 A | 4/1992 | Shewmaker et al. | 800/205 |
| 5,356,799 A | 10/1994 | Fabijanski et al. | 435/172.3 |
| 5,478,369 A | 12/1995 | Albertsen et al. | 47/58 |
| 5,689,051 A | 11/1997 | Cigan et al. | 800/205 |
| 5,728,558 A | 3/1998 | Fabijanski et al. | 435/172.3 |
| 5,728,926 A | 3/1998 | Fabijanski et al. | 800/205 |
| 5,741,684 A | 4/1998 | Fabijanski et al. | 435/172.3 |

OTHER PUBLICATIONS

Buckingham et al, "Nucleotide sequence and promoter analysis of SPO13, a meiosis–specific gene of *Saccharomyces cerevisiae*", Dec. 1990, Proc. Natl. Acad. vol. 87, pp. 9406–9410.*

\* cited by examiner

*Primary Examiner*—Phuong T. Bui
*Assistant Examiner*—Medina A. Ibrahim
(74) *Attorney, Agent, or Firm*—Heslin Rothenberg Farley & Mesiti P.C.

(57) ABSTRACT

A novel meiosis-specific gene sequence from *Arabidopsis thaliana* including the promoter region is described. When operably linked to a heterologous gene or to the antisense of the MEI1 gene, the normal meiotic events which give rise to viable pollen can be altered. Transgenic male sterile plants can thereby be produced by the manipulation of gene expression using a genetic regulatory element such as the one described herein.

15 Claims, 5 Drawing Sheets

FIGURE 1

```
-2911  ACTTTGGAAC CCACCATGGC ATTCAATAGT AAAATGTGCG TTATTTATCA
-2861  AAGGATCATT ACCACCTCTC CCCCTCCTTG ATTCACCCAT TCCACGATTT
-2811  GCGGTCGCTG CACAAATTGG TAACACATCA ATCAATAGAC CTCGGAGATG
-2761  CATTCTCAGA CAAGAAACTA GTGCAAAACA AGGAAAATTG ATTTGATAA
-2711  CCACATACCC TATCTTCAGG AAAAGAATGC GAGAAACAAA ATGTTTCCCC
-2661  CTTAAATACA GATGACTTTC TTTCTTGATC GTTCTGACCA CTGAATTCAC
-2611  ATTGAATACT CCGTTGTTCT TTGCTTTCAC AAGTTACAAG TTGAATAAGT
-2561  GTTTCTTTTT GCGTGGGTGA TACTATTTTT CTTCCTGTAT GAATCTCATC
-2511  TTTTCTGCCA AATTCCTGCA TTGCTTCTTT GTTTTTTCCC AGTAAAGTTN
-2461  CTGGCCCATT TGAGACATTG ATACTCCTTG AAGAAGAATC ATATACCATG
-2411  GTCTGGTCGT GAGTATTTTT AGTCTGTTCC ATACTTGACA TCCTTNCAAA
-2361  TGACCCCTTG GTCAAGCATG CAGAATCTGC ACACAAAAAA AAGTCACTTA
-2311  GAAAAGTGTA ATATAACGCA TTGATATGTC TTGATGCATA TTAGATAGAT
-2261  GACATGTGTC TGAGATAATT AAAAAATGGT TAAATGAGAT AACAGCAGAC
-2211  CTCTTGGAAG AATCAAGTGG TTAGCAGTAT ATATATNATG AACGGGATT
-2161  TCTTTTTTCT CACGATCACA ATCTTCAAGC CAACTGGGTA TGACTACTTG
-2111  AATGACACCA GAAGCTGCAA CACTCCTTGC TTCTCTTTTC TCACTACAAA
-2061  AGAATATTTA TGTAGAGATC ATTATGTTAC AGAGAATATG CTTAGAGAGA
-2011  CCCACCTAAC AGAACTCGAC CAATGCTACA AGAGAAAAAA GGAAAAAGCT
-1961  GATAGAGCAA AATCGAACCC AATGTTTACC TCTCTGAAGG AGTTCCAACA
-1911  ACAATATGAG TCATTCTTTC GTTAAGCAGC ATATACCGGG ATCCACCACC
-1861  TCTGCGGACC AACTTAGCAA GTTTACGCAT TCAGAAGCT TCAAAACCAA
-1811  GCAAGAAAAT TCTACAATCT GATAAGTACA AGTCATTGTC TTCGGATTCT
-1761  GAATCCCTGG CAGTACAACC ATCAATGTTT TGCTCTTGCG CCTTGCCGTT
-1711  GGGCCTCCAC CTGGTTCTTT AACATCGGTA CTGGGATTCA TAGAAGTGGG
```

FIGURE 1

```
-1661  AAAAACATTT TGTGAAGCAG AAGCTTCTAT ATCTGAGTCT CTAGACTGAG
-1611  CACAAGAAAC ATATGAATCT GCCGCGGACG CAGTTGCAGC CGAAGGAAAC
-1561  TTTTCTAGAC CATTATGACC CCCAAATCTC GCACTCCTCT TGTCAAGGTA
-1511  TGGAACCGAG AACAGGATAT GACTCTTCAT TGAGACAAAC TGCGCATAAC
-1461  AAGGTGACAT ATCAGTATCG AATGAATCTG TTAACTTATA GAGAGCCAAT
-1411  ATACCGATCA CTGATCAGTA AGAGAATGTA TAAAATGCAG AAGCACCCAA
-1361  CGTCACCCTT TTTATCGATG GACTGCTGAA ACCATTTCCG TGTGACAATT
-1311  TGAATGTGAC CCCATTTTCG AGCAACTTTG TATTTGTCAC CTTCAGCAGC
-1261  GTATGCAAGG TCAAGGAATC ATTTTTCATT AAAGTCCAAA TAACGCAACC
-1211  TCAAACTTTA GTGCACAGGA ACTTGGAATT TAAGGCATCT ATATATCAAC
-1161  CACGTAATGG TTATATTCAC ATATCTTGTA ACTTCAGAGA ACCCGATTGG
-1111  TAAGCCTTGA ATACTGCTAA TTTATCAGCA CAACTGAATG CGCACACAAA
-1061  ATCAACATAT GTCCTAGGAA TAGCACATTT TTAAATTTTG TTTCAAGGA
-1011  TATATCAGCG ATCAAATGTG TACAACTCTT TGTTAGCTCA GCAGAGTAGC
 -961  TCCCTCCATA TTCTGAAATT ACCTTTTCCA TTCCCTTGCG TTCATCTGAT
 -911  AATAAATCAC TGATTAACTG TCAACAAAGA ACCTAATTCG CATATGTTGA
 -861  ATATACCGGT TTTCTAACCT GCTGGAATTC TTGTGACACA GATTGTCAAT
 -811  CCAGAAAAAG GAGGAATCTT ATATGGTTCC TGAGGAACCA CACGGTGCTC
 -761  ATTCCAACAC CGATGTAACC AATTCAGAGT AACGATTGGC TTCTTATTCA
 -711  GGGCCCACTG CAAGTTAAAA TAAGATATAT TTATCAGACC CAATGAAATA
 -661  GGCATAACAG CTTCCTCATG AACCTCATCA GTTCACTCTG CTCTAGGATA
 -611  TATATGTAAT GATAAGTCAG TAGAGGCACG ACGCTGACTA AAAATAATTT
 -561  CAGAAAACAA CGGTGTTTTT CACTCTGAGA AGTAAACCTG CAATCCTGCA
 -511  TTAGCCTAAG TATTATATAC ATCATCCAGC TACCATCTAA AATGAACAAA
 -461  GCAGAACCCG TCAATAGGGG GATGACGACA ACCTATATTT TGAGGCCTTC
 -411  ATTAGGGGCA TTTTACATCT TTACTTACGC GAAAAGGCCT CTCTTCTTTT
 -361  AATGTAGGCA CTATGTACTG CTGGGAAAAT GTAATTTCTC ACATGCACCG
```

FIGURE 1

```
-311  TGCAAAAGAT CAACAGCCAC TTCTATGATT CTATCTAACT TTAATTTACC

-261  GGCATCGACA GAGAAAATT CATCTAATTG GGGTAAAGCT AAATGAACTG

-211  ATAACACTTT TAGTTTATCT AACATAGTTG GAATAATTTT CTGAGATGCA

-161  TTATGGAAAA CAGCGGTATT GATATGTTAC TAAAGCAAAG GTGAAACTGA

-111  TAAGAAGCTA GTTATATAAT CTACAGATGT GAACCTTCAG AAGGTAAAAG

-61  AATATTGATC GCAATCTTTG AACAATAGAC CTTGTACTTG GCAGCCAAGA
                                --->
 -11  CATTTTTCAC AATGACGAAG TTCACATCAG AAGAAGCTCT GGAAAGTAAA
                 M  T  K    F  T  S    E  E  A  L    E  S  K

40  ACGCCCCCA TGGAAGTAAC CAACTCCTTG ATCTTGACct tcaaaagaat
       T P P     M  E  V  T   N  S  L   I  L  T 90  tgcaatcaat caattaagag ggattagtcc ttcagagtaa ctgaaaaaac 140  aattccctca acagaaatca tttttaatc tacatgcttc gtacactcta 190  aaaacacatt tcaactaaat caaagagag gtcagttttt ttcttttaac 240  acagaaattg aaccataaac caaaatttct aaaattgttt agttgcgcaa 290  tgggaaacaa agagacacaa gtattcaata ctatgtcata tgcacactgt 340  taatctcata atcgataggt gaacgaacat agactcacaa ccattcccat 390  ggagattaca gtacaagggg aataaggat actaataaac taaaaacgac 440  atctattaca ctgacaaaag aagtacCTTC TCATCTACCA GAAAACCAGA
                                    F  S  S  T  R    K  P  E 490  AGCAAGAACT TTTAGACCAT CCATGGCTAG GCAACAAGTG AATCCCCTTT
       A  R  T    F  R  P    S  M  A  R   Q  Q  V   N  P  L 540  GTGGCAGTGG TCTACCCTCT TTTGCACAGA AGAGCGCACA TTGCGGACct
       C  G  S  G   L  P  S  F  A  Q    K  S  A  H    C  G 590  gccacgcaat aaacataaat ccaattaaga aaattcacaa acacagaatc 640  aattgattta ttaagtgaca agaaatataa aataaatctc atctcacCTA
                                                            P 690  TTAAGTTACA ACCCTTGGCT TTAAGATCCT TAAATTTCTC CTGTAAAACC
       I  K  L  Q    P  L  A  L  R  S   L  N  F  S   C  K  T 740  CCAAAAAAAT GGCAATAAGA GCAGTTATAT AACGAAATAA GCAATTGCAG
       P  K  K    W  Q  *

790  GATATATAAG AAAGAACATT TCGCACATGA TCGGGAGAAG CGATGACATG
```

Figure 1

```
 840   GAAATCAGAG  GGACCACTCC  GAGATGGGTC  GCAGCAGAGG  AAGATTTCGG
 890   CACCGTTAAG  CTTGAAAGCA  TCGAGAAGTG  TGTCGAAGAC  TTCAGGAGGC
 940   ACCAGATTCC  GAGACATAAA  AACATTTGCC  CCTTTGAACA  GTTGCGTCGT
 990   CTTCATCGCC  GCCGGAAAAC  CTAACCACGC  ACTTCTCGAC  TTTGTAAGAG
1040   CTTCACGGGG  TTATCGGAGA  AAATTGAAAC  CCTAGAATCG  TCGGAAGAAG
1090   ATGGATATTA  GAACCTAGTA  GCATTCGCAT  AGCACGAGAT  TCGTCAAGCT
1140   CTGGATTTGA  GGTCAGTATT  CGGCGTGGTA  ACTGGTAAGA  AGAGAACGCG
1190   GGAATTTTCG  GTGCGCTTTT  TTTTGGTCG   TCCAGTCCAG  TGAGCTTGAT
1240   TTCAGATACA  TACTAATTCC  TTTTTAAGGC  TTTTTATTCT  TTTATTATGA
1290   CCCCTTATTG  GGCCGCCGAC  AAATTTAGAC  CCATTTAGAA  ATAGGCTACA
1340   TGTGTTGGTT  TATactttat  TCCGTCAAAA  AAAACAGATT  GAAAGAATTG
1390   GAGCTTCTCT  TAACATCTTT  AATTTGTAAC  GAGGAGAGGG  ACTTCGTCTT
1440   CTACGTAAGA  AACGACTAGA  AAATCAATAC  TAGGCGCAAA  AATTAGAAGC
1490   GAAACTATAG  CTACGAAAAA  CAAAGGCAAG  GCTAGAGCCA  GACTTTGAGA
1540   AAAAAAATCT  AAGCTGTAGT  ACCTAACTTG  GCAGGTTCAG  GTCTGGAGGA
```

FIG. 2

SEQUENCE LISTING

<160> NUMBER OF SEQ ID NOS: 19

<210> SEQ ID NO 1
<211> LENGTH: 4500
<212> TYPE: DNA
<213> ORGANISM: Arabidopsis thaliana
<220> FEATURE:
<221> NAME/KEY: allele
<222> LOCATION: (450)
<223> OTHER INFORMATION: n may be C,G,T or A
<221> NAME/KEY: allele
<222> LOCATION: (546)
<223> OTHER INFORMATION: n may be C,G,T or A
<221> NAME/KEY: allele
<222> LOCATION: (737)
<223> OTHER INFORMATION: n may be C,G,T or A

<400> SEQUENCE: 1

```
actttggaac ccaccatggc attcaatagt aaaatgtgcg ttatttatca aaggatcatt      60
accacctctc cccctccttg attcacccat tccacgattt gcggtcgctg cacaaattgg     120
taacacatca atcaatagac ctcggagatg cattctcaga caagaaacta gtgcaaaaca     180
aggaaaattg attttgataa ccacataccc tatcttcagg aaaagaatgc gagaaacaaa     240
atgtttcccc cttaaataca gatgactttc tttcttgatc gttctgacca ctgaattcac     300
attgaatact ccgttgttct ttgctttcac aagttacaag ttgaataagt gtttcttttt     360
gcgtggtga tactattttt cttcctgtat gaatctcatc ttttctgcca aattcctgca     420
ttgcttcttt gttttttccc agtaaagttn ctggcccatt tgagacattg atactccttg     480
aagaagaatc ataccatg gtctggtcgt gagtattttt agtctgttcc atacttgaca       540
tccttncaaa tgaccccttg gtcaagcatg cagaatctgc acacaaaaaa aagtcactta     600
gaaagtgta atataacgca ttgatatgtc ttgatgcata ttagatagat gacatgtgtc      660
tgagataatt aaaaaatggt taaatgagat aacagcagac ctcttggaag aatcaagtgg     720
ttagcagtat atatatnatg aacggggatt tcttttttct cacgatcaca atcttcaagc     780
caactgggta tgactacttg aatgacacca gaagctgcaa cactccttgc ttctcttttc     840
tcactacaaa agaatattta tgtagagatc attatgttac agagaatatg cttagagaga     900
cccacctaac agaactcgac caatgctaca agagaaaaaa ggaaaaagct gatagagcaa     960
aatcgaaccc aatgtttacc tctctgaagg agttccaaca acaatatgag tcattctttc    1020
gttaagcagc ataccgggg atccaccacc tctgcggacc aacttagcaa gtttacgcat     1080
ttcagaagct tcaaaaccaa gcaagaaaat tctacaatct gataagtaca agtcattgtc    1140
ttcggattct gaatccctgg cagtacaacc atcaatgttt tgctcttgcg ccttgccgtt    1200
gggcctccac ctggttcttt aacatcggta ctgggattca tagaagtggg aaaaacattt    1260
tgtgaagcag aagcttctat atctgagtct ctagactgag cacaagaaac atatgaatct    1320
gccgcggacg cagttgcagc cgaaggaaac ttttctagac cattatgacc cccaaatctc    1380
gcactcctct tgtcaaggta tggaaccgag aacaggatat gactcttcat tgagacaaac    1440
tgcgcataac aaggtgacat atcagtatcg aatgaatctg ttaacttata gagagccaat    1500
ataccgatca ctgatcagta agagaatgta taaaatgcag aagcacccaa cgtcacccett    1560
tttatcgatg gactgctgaa accatttccg tgtgacaatt tgaatgtgac cccatttttcg    1620
agcaactttg tatttgtcac cttcagcagc gtatgcaagg tcaaggaatc attttttcatt    1680
aaagtccaaa taacgcaacc tcaaacttta gtgcacagga acttggaatt taaggcatct    1740
```

```
atatatcaac cacgtaatgg ttatattcac atatcttgta acttcagaga acccgattgg    1800
taagccttga atactgctaa tttatcagca caactgaatg cgcacacaaa atcaacatat    1860
gtcctaggaa tagcacattt ttaaattttg tttcaaagga tatatcagcg atcaaatgtg    1920
tacaactctt tgttagctca gcagagtagc tccctccata ttctgaaatt acctttccca    1980
ttcccttgcg ttcatctgat aataaatcac tgattaactg tcaacaaaga acctaattcg    2040
catatgttga ataccggt tttctaacct gctggaattc ttgtgacaca gattgtcaat      2100
ccagaaaaag gaggaatctt tatggttcc tgaggaacca cacggtgctc attccaacac     2160
cgatgtaacc aattcagagt aacgattggc ttcttattca gggcccactg caagttaaaa    2220
taagatatat ttatcagacc caatgaaata ggcataacac cttcctcatg aacctcatca    2280
gttcactctg ctctaggata tatatgtaat gataagtcag tagaggcacg acgctgacta    2340
aaaataattt cagaaaacaa cggtgttttt cactctgaga agtaaacctg caatcctgca    2400
ttagcctaag tattatatac atcatccagc taccatctaa aatgaacaaa gcagaacccg    2460 tcaataggg gatgacgaca acctatattt tgaggccttc attaggggca ttttacatct     2520
ttacttacgc gaaaaggcct ctcttctttt aatgtaggca ctatgtactg ctgggaaaat    2580
gtaatttctc acatgcaccg tgcaaaagat caacagccac ttctatgatt ctatctaact    2640
ttaatttacc ggcatcgaca gagaaaaatt catctaattg gggtaaagct aaatgaactg    2700
ataacacttt tagtttatct aacatagttg aataattttt ctgagatgca ttatggaaaa    2760
cagcggtatt gatatgttac taaagcaaag gtgaaactga taagaagcta gttatataat    2820
ctacagatgt gaaccttcag aaggtaaaag aatattgatc gcaatctttg aacaatagac    2880
cttgtacttg gcagccaaga catttttcac a atg acg aag ttc aca tca gaa gaa  2935
                                  Met Thr Lys Phe Thr Ser Glu Glu
                                   1               5 gct ctg gaa agt aaa acg ccc ccc atg gaa gta acc aac tcc ttg atc      2983
Ala Leu Glu Ser Lys Thr Pro Pro Met Glu Val Thr Asn Ser Leu Ile
     10              15                  20 ttg acc ttcaaaagaa ttgcaatcaa tcaattaaga gggattagtc cttcagagta       3039
Leu Thr
 25 actgaaaaaa caattccctc aacagaaatc attttttaat ctacatgctt cgtacactct    3099 aaaaacacat ttcaactaaa tcaaaagaga ggtcagtttt tttcttttaa cacagaaatt    3159 gaaccataaa ccaaaatttc taaaattgtt tagttgcgca atgggaaaca aagagacaca    3219 agtattcaat actatgtcat atgcacactg ttaatctcat aatcgatagg tgaacgaaca    3279 tagactcaca accattccca tggagattac agtacaaggg gaataaagga tactaataaa    3339 ctaaaaacga catctattac actgacaaaa gaagtacc ttc tca tct acc aga       3392
                                           Phe Ser Ser Thr Arg
                                                          30 aaa cca gaa gca aga act ttt aga cca tcc atg gct agg caa caa gtg      3440
Lys Pro Glu Ala Arg Thr Phe Arg Pro Ser Met Ala Arg Gln Gln Val
         35                  40                  45 aat ccc ctt tgt ggc agt ggt cta ccc tct ttt gca cag aag agc gca      3488
Asn Pro Leu Cys Gly Ser Gly Leu Pro Ser Phe Ala Gln Lys Ser Ala
     50                  55                  60 cat tgc gga cctgccacgc aataaacata aatccaatta agaaaattca caaacacaga   3547
His Cys Gly
         65 atcaattgat ttattaagtg acaagaaata taaaataaat ctcatctca cct att aag    3605
                                                      Pro Ile Lys
```

-continued

```
tta caa ccc ttg gct tta aga tcc tta aat ttc tcc tgt aaa acc cca    3653
Leu Gln Pro Leu Ala Leu Arg Ser Leu Asn Phe Ser Cys Lys Thr Pro
 70                  75                  80                  85 aaa aaa tgg caa taaga gcagttatat aacgaaataa gcaattgcag gatatataag   3710
Lys Lys Trp Gln aaagaacatt tcgcacatga tcgggagaag cgatgacatg gaaatcagag ggaccactcc   3770
gagatgggtc gcagcagagg aagatttcgg caccgttaag cttgaaagca tcgagaagtg   3830
tgtcgaagac ttcaggaggc accagattcc gagacataaa aacatttgcc cctttgaaca   3890
gttgcgtcgt cttcatcgcc gccggaaaac ctaaccacgc acttctcgac tttgtaagag   3950
cttcacgggg ttatcggaga aaattgaaac cctagaatcg tcggaagaag atggatatta   4010
gaacctagta gcattcgcat agcacgagat tcgtcaagct ctggatttga ggtcagtatt   4070
cggcgtggta actggtaaga agagaacgcg ggaattttcg gtgcgctttt ttttggtcg    4130 tccagtccag tgagcttgat ttcagataca tactaattcc tttttaaggc tttttattct   4190
tttattatga cccctattg ggccgccgac aaatttagac ccatttagaa ataggctaca    4250
tgtgttggtt tatactttat tccgtcaaaa aaaacagatt gaaagaattg gagcttctct   4310
taacatcttt aatttgtaac gaggagaggg acttcgtctt ctacgtaaga aacgactaga   4370
aaatcaatac taggcgcaaa aattagaagc gaaactatag ctacgaaaaa caaaggcaag   4430
gctagagcca gactttgaga aaaaaaatct aagctgtagt acctaacttg gcaggttcag   4490
gtctggagga                                                          4500
```

```
<210> SEQ ID NO 2
<211> LENGTH: 24
<212> TYPE: DNA
<213> ORGANISM: Artificial sequence
<220> FEATURE:
<223> OTHER INFORMATION: designed primer corresponding to T-DNA right
      border in opposite orientation to that for normal PCR

<400> SEQUENCE: 2
ttaattgttg ccgggaagct agag                                            24

<210> SEQ ID NO 3
<211> LENGTH: 20
<212> TYPE: DNA
<213> ORGANISM: Artificial sequence
<220> FEATURE:
<223> OTHER INFORMATION: designed primer corresponding to T-DNA right
      border in opposite orientation to that for normal PCR

<400> SEQUENCE: 3
caaccttccg gcgttcgtgg                                                 20

<210> SEQ ID NO 4
<211> LENGTH: 30
<212> TYPE: DNA
<213> ORGANISM: Artificial sequence
<220> FEATURE:
<223> OTHER INFORMATION: designed primer corresponding to T-DNA
      insertion region

<400> SEQUENCE: 4
cggtctcgag atcttcctct gctgcgaccc                                      30

<210> SEQ ID NO 5
<211> LENGTH: 31
<212> TYPE: DNA
```

```
<213> ORGANISM: Artificial sequence
<220> FEATURE:
<223> OTHER INFORMATION: designed primer corresponding to T-DNA
      insertional region

<400> SEQUENCE: 5
ttgggatccg cagccaagac atttttcaca a                              31

<210> SEQ ID NO 6
<211> LENGTH: 30
<212> TYPE: DNA
<213> ORGANISM: Artificial sequence
<220> FEATURE:
<223> OTHER INFORMATION: designed primer

<400> SEQUENCE: 6
gaagatctgg tagatgagaa ggtcaagatc                                30

<210> SEQ ID NO 7
<211> LENGTH: 25
<212> TYPE: DNA
<213> ORGANISM: Artificial sequence
<220> FEATURE:
<223> OTHER INFORMATION: designed primer

<400> SEQUENCE: 7
cggattctga tcgcaatctt tgaac                                     25

<210> SEQ ID NO 8
<211> LENGTH: 7
<212> TYPE: DNA
<213> ORGANISM: Saccharomyces cerevisiae

<400> SEQUENCE: 8 uacuaac                                                          7

<210> SEQ ID NO 9
<211> LENGTH: 5
<212> TYPE: DNA
<213> ORGANISM: Arabidopsis thaliana

<400> SEQUENCE: 9 ctgac                                                            5

<210> SEQ ID NO 10
<211> LENGTH: 5
<212> TYPE: DNA
<213> ORGANISM: Arabidopsis thaliana

<400> SEQUENCE: 10 ctaaa                                                            5

<210> SEQ ID NO 11
<211> LENGTH: 5
<212> TYPE: DNA
<213> ORGANISM: Arabidopsis thaliana

<400> SEQUENCE: 11 ctaat                                                            5

<210> SEQ ID NO 12
<211> LENGTH: 5
<212> TYPE: DNA
<213> ORGANISM: Arabidopsis thaliana
```

-continued

```
<400> SEQUENCE: 12 ctcat                                                                      5

<210> SEQ ID NO 13
<211> LENGTH: 5
<212> TYPE: DNA
<213> ORGANISM: Arabidopsis thaliana

<400> SEQUENCE: 13 ttaag                                                                      5

<210> SEQ ID NO 14
<211> LENGTH: 5
<212> TYPE: DNA
<213> ORGANISM: Arabidopsis thaliana

<400> SEQUENCE: 14 tttat                                                                      5

<210> SEQ ID NO 15
<211> LENGTH: 5
<212> TYPE: DNA
<213> ORGANISM: Arabidopsis thaliana

<400> SEQUENCE: 15 ttgat                                                                      5

<210> SEQ ID NO 16
<211> LENGTH: 2911
<212> TYPE: DNA
<213> ORGANISM: Arabidopsis thaliana
<220> FEATURE:
<221> NAME/KEY: promoter
<222> LOCATION: (1)...(2911)
<221> NAME/KEY: allele
<222> LOCATION: (450)
<223> OTHER INFORMATION: n may be C,G,T or A
<221> NAME/KEY: allele
<222> LOCATION: (546)
<223> OTHER INFORMATION: n may be C,G,T or A
<221> NAME/KEY: allele
<222> LOCATION: (737)
<223> OTHER INFORMATION: n may be C,G,T or A

<400> SEQUENCE: 16
actttggaac ccaccatggc attcaatagt aaaatgtgcg ttatttatca aaggatcatt         60
accacctctc cccctccttg attcacccat tccacgattt gcggtcgctg cacaaattgg        120
taacacatca atcaatagac ctcggagatg cattctcaga caagaaacta gtgcaaaaca        180
aggaaaattg attttgataa ccacataccc tatcttcagg aaaagaatgc gagaaacaaa        240
atgtttcccc cttaaataca gatgactttc tttcttgatc gttctgacca ctgaattcac        300
attgaatact ccgttgttct tgctttcac aagttacaag ttgataagt gtttcttttt          360 gcgtgggtga tactatttt cttcctgtat gaatctcatc ttttctgcca aattcctgca         420
ttgcttcttt gtttttccc agtaaagttn ctggcccatt tgagacattg atactccttg         480
aagaagaatc ataccatg gtctggtcgt gagtattttt agtctgttcc atacttgaca          540
tccttncaaa tgaccccttg gtcaagcatg cagaatctgc acacaaaaaa aagtcactta        600
gaaaagtgta atataacgca ttgatatgtc ttgatgcata ttagatagat gacatgtgtc        660
tgagataatt aaaaaatggt taaatgagat aacagcagac ctcttggaag aatcaagtgg        720
ttagcagtat atatatnatg aacggggatt tcttttttct cacgatcaca atcttcaagc        780
```

```
caactgggta tgactacttg aatgacacca gaagctgcaa cactccttgc ttctcttttc     840
tcactacaaa agaatattta tgtagagatc attatgttac agagaatatg cttagagaga     900
cccacctaac agaactcgac caatgctaca agagaaaaaa ggaaaaagct gatagagcaa     960
aatcgaaccc aatgtttacc tctctgaagg agttccaaca acaatatgag tcattctttc    1020
gttaagcagc atataccggg atccaccacc tctgcgacca acttagcaa gtttacgcat      1080
ttcagaagct tcaaaaccaa gcaagaaaat tctacaatct gataagtaca agtcattgtc    1140
ttcggattct gaatccctgg cagtacaacc atcaatgttt tgctcttgcg ccttgccgtt    1200
gggcctccac ctggttcttt aacatcggta ctgggattca tagaagtggg aaaaacattt    1260
tgtgaagcag aagcttctat atctgagtct ctagactgag cacaagaaac atatgaatct    1320
gccgcggacg cagttgcagc cgaaggaaac ttttctagac cattatgacc cccaaatctc    1380
gcactcctct tgtcaaggta tggaaccgag aacaggatat gactcttcat tgagacaaac    1440
tgcgcataac aaggtgacat atcagtatcg aatgaatctg ttaacttata gagagccaat    1500
ataccgatca ctgatcagta agagaatgta taaaatgcag aagcacccaa cgtcacccct    1560
tttatcgatg gactgctgaa accatttccg tgtgacaatt tgaatgtgac cccatttcg     1620
agcaactttg tatttgtcac cttcagcagc gtatgcaagg tcaaggaatc atttttcatt    1680
aaagtccaaa taacgcaacc tcaaacttta gtgcacagga acttggaatt taaggcatct    1740
atatatcaac cacgtaatgg ttatattcac atatcttgta acttcagaga acccgattgg    1800
taagccttga atactgctaa tttatcagca caactgaatg cgcacacaaa atcaacatat    1860
gtcctaggaa tagcacattt ttaaattttg tttcaaagga tatatcagcg atcaaatgtg    1920
tacaactctt tgttagctca gcagagtagc tccctccata ttctgaaatt accttttcca    1980
ttcccttgcg ttcatctgat aataaatcac tgattaactg tcaacaaaga acctaattcg    2040
catatgttga atataccggt tttctaacct gctggaattc ttgtgacaca gattgtcaat    2100
ccagaaaaag gaggaatctt atatggttcc tgaggaacca cacggtgctc attccaacac    2160
cgatgtaacc aattcagagt aacgattggc ttcttattca gggcccactg caagttaaaa    2220
taagatatat ttatcagacc caatgaaata ggcataacag cttcctcatg aacctcatca    2280
gttcactctg ctctaggata tatatgtaat gataagtcag tagaggcacg acgctgacta    2340
aaaataattt cagaaaacaa cggtgttttt cactctgaga agtaaacctg caatcctgca    2400
ttagcctaag tattatatac atcatccagc taccatctaa aatgaacaaa gcagaacccg    2460
tcaataggggg gatgacgaca acctatattt tgaggccttc attagggggca ttttacatct   2520
ttacttacgc gaaaaggcct ctcttctttt aatgtaggca ctatgtactg ctgggaaaat    2580
gtaatttctc acatgcaccg tgcaaaagat caacagccac ttctatgatt ctatctaact    2640
ttaatttacc ggcatcgaca gagaaaaatt catctaattg gggtaaagct aaatgaactg    2700
ataacacttt tagtttatct aacatagttg gaataatttt ctgagatgca ttatggaaaa    2760
cagcggtatt gatatgttac taaagcaaag gtgaaactga taagaagcta gttatataat    2820
ctacagatgt gaaccttcag aaggtaaaag aatattgatc gcaatctttg aacaatagac    2880
cttgtacttg gcagccaaga cattttttcac a                                  2911
```

<210> SEQ ID NO 17
<211> LENGTH: 1589
<212> TYPE: DNA
<213> ORGANISM: Arabidopsis thaliana
<220> FEATURE:

<221> NAME/KEY: gene
<222> LOCATION: (1)...(1589)

<400> SEQUENCE: 17

| | | | | | |
|---|---|---|---|---|---|
| atgacgaagt | tcacatcaga | agaagctctg | gaaagtaaaa | cgcccccat | 60 |
| aactccttga | tcttgacctt | caaaagaatt | gcaatcaatc | aattaagagg | gattagtcct | 120 |
| tcagagtaac | tgaaaaaaca | attccctcaa | cagaaatcat | tttttaatct | acatgcttcg | 180 |
| tacactctaa | aaacacattt | caactaaatc | aaaagagagg | tcagtttttt | tcttttaaca | 240 |
| cagaaattga | accataaacc | aaaatttcta | aaattgttta | gttgcgcaat | gggaaacaaa | 300 |
| gagacacaag | tattcaatac | tatgtcatat | gcacactgtt | aatctcataa | tcgataggtg | 360 |
| aacgaacata | gactcacaac | cattcccatg | gagattacag | tacaagggga | ataaaggata | 420 |
| ctaataaact | aaaaacgaca | tctattacac | tgacaaaaga | agtaccttct | catctaccag | 480 |
| aaaaccagaa | gcaagaactt | ttagaccatc | catggctagg | caacaagtga | atcccctttg | 540 |
| tggcagtggt | ctaccctctt | ttgcacagaa | gagcgcacat | tgcggacctg | ccacgcaata | 600 |
| aacataaatc | caattaagaa | aattcacaaa | cacagaatca | attgatttat | taagtgacaa | 660 |
| gaaatataaa | ataaatctca | tctcacctat | taagttacaa | cccttggctt | taagatcctt | 720 |
| aaatttctcc | tgtaaaaccc | caaaaaaatg | gcaataagca | cagttatata | acgaaataag | 780 |
| caattgcagg | atatataaga | agaacatttt | cgcacatgat | cgggagaagc | gatgacatgg | 840 |
| aaatcagagg | gaccactccg | agatgggtcg | cagcagagga | agatttcggc | accgttaagc | 900 |
| ttgaaagcat | cgagaagtgt | gtcgaagact | tcaggaggca | ccagattccg | agacataaaa | 960 |
| acatttgccc | ctttgaacag | ttgcgtcgtc | ttcatcgccg | ccggaaaacc | taaccacgca | 1020 |
| cttctcgact | ttgtaagagc | ttcacggggt | tatcggagaa | aattgaaacc | ctagaatcgt | 1080 |
| cggaagaaga | tggatattag | aacctagtag | cattcgcata | gcacgagatt | cgtcaagctc | 1140 |
| tggatttgag | gtcagtattc | ggcgtggtaa | ctggtaagaa | gagaacgcgg | gaattttcgg | 1200 |
| tgcgcttttt | ttttggtcgt | ccagtccagt | gagcttgatt | tcagatacat | actaattcct | 1260 |
| ttttaaggct | ttttattctt | ttattatgac | cccttattgg | gccgccgaca | aatttagacc | 1320 |
| catttagaaa | taggctacat | gtgttggttt | atactttatt | ccgtcaaaaa | aaacagattg | 1380 |
| aaagaattgg | agcttctctt | aacatcttta | atttgtaacg | aggagaggga | cttcgtcttc | 1440 |
| tacgtaagaa | acgactagaa | aatcaatact | aggcgcaaaa | attagaagcg | aaactatagc | 1500 |
| tacgaaaaac | aaaggcaagg | ctagagccag | actttgagaa | aaaaaatcta | agctgtagta | 1560 |
| cctaacttgg | caggttcagg | tctggagga | | | 1589 |

<210> SEQ ID NO 18
<211> LENGTH: 270
<212> TYPE: DNA
<213> ORGANISM: Arabidopsis thaliana
<220> FEATURE:
<221> NAME/KEY: CDS
<222> LOCATION: (1)...(270)

<400> SEQUENCE: 18

| | | | | | |
|---|---|---|---|---|---|
| atgacgaagt | tcacatcaga | agaagctctg | gaaagtaaaa | cgcccccat | ggaagtaacc | 60 |
| aactccttga | tcttgacctt | ctcatctacc | agaaaaccag | aagcaagaac | ttttagacca | 120 |
| tccatggcta | ggcaacaagt | gaatcccctt | gtggcagtg | gtctaccctc | ttttgcacag | 180 |
| aagagcgcac | attgcggacc | tattaagtta | caacccttgg | ctttaagatc | cttaaatttc | 240 |
| tcctgtaaaa | ccccaaaaaa | atggcaataa | | | 270 |

```
<210> SEQ ID NO 19
<211> LENGTH: 89
<212> TYPE: PRT
<213> ORGANISM: Arabidopsis thaliana

<400> SEQUENCE: 19

Met Thr Lys Phe Thr Ser Glu Glu Ala Leu Glu Ser Lys Thr Pro Pro
1               5                   10                  15

Met Glu Val Thr Asn Ser Leu Ile Leu Thr Phe Ser Ser Thr Arg Lys
            20                  25                  30

Pro Glu Ala Arg Thr Phe Arg Pro Ser Met Ala Arg Gln Gln Val Asn
                35                  40                  45

Pro Leu Cys Gly Ser Gly Leu Pro Ser Phe Ala Gln Lys Ser Ala His
        50                  55                  60

Cys Gly Pro Ile Leu Lys Gln Pro Leu Ala Leu Arg Ser Leu Asn Phe
65                  70                  75                  80

Ser Cys Lys Thr Pro Lys Lys Trp Gln
                85
```

MEIOSIS PROMOTER

CROSS REFERENCE TO RELATED APPLICATION

This application claims the priority of U.S. provisional application No. 60/092,277, filed Jul. 10, 1998, the entire disclosure of which is incorporated herein by reference.

STATEMENT OF RIGHTS UNDER FEDERALLY-SPONSORED RESEARCH

This invention was made with government support under grant IBN-9208337 awarded by The National Science Foundation. The government has certain rights in the invention.

FIELD OF THE INVENTION

This invention relates generally to the field of recombinant genetics, and specifically to the use of a meiosis-specific promoter for regulating the expression of genes in plants. More particularly, the invention enables the expression of desired introduced genes in transgenic plants to be controlled in a developmentally related manner.

BACKGROUND OF THE INVENTION

To optimize crop production, the agricultural industry relies on plants having certain desirable traits relating to growth characteristics, resistance to disease and pest infestation, and yield.

One way to attain this goal is to produce hybrid plants possessing the desirable traits of parental plants. To insure the uniformity of hybrid seed, pollination control methods must be employed which favor cross-pollination and eliminate self-pollination. Such methods of inhibiting self-pollination of plants typically include mechanical means, as well as chemical.

Mechanical means such as detasseling, the process currently used for plants such as corn, is labor intensive and costly to perform. For some plants, for example those whose male and female gametophytes are within the same flower, the method is even less desirable.

As an alternative to mechanical methods to prevent self pollination, chemicals which kill or inhibit formation of functional pollen may be used. Application of chemicals, however, may result in overall toxicity to the plant or to the environment. Another limitation of the chemical means is the possibility that one application will not be effective for plants which have an extended period of flower formation.

More recently, the industry has relied on pollen-control-based systems which involve genetic manipulation of the events involved in the development of functional pollen. One example is described in U.S. Pat. No. 5,689,051, the contents of which are hereby incorporated by reference in their entirety. Briefly, regulatory elements are described which alter the expression of genes involved in pollen development. The ability to interfere with the production or formation of pollen results in a plant that is male sterile and therefore, incapable of self-pollination.

Similarly, it is possible to control plant characteristics other than pollen development by manipulating the control of gene expression which gives rise to the desired phenotype. An example of this technology is illustrated in U.S. Pat. No. 5,723,765. It discloses a system in which the expression of genes can be controlled by external stimuli or in a developmentally related fashion. The system entails creating a transgenic plant containing a series of functionally interrelated DNA sequences, including a promoter that is active at a particular stage in plant development or in response to an external stimulus, for example, a particular environmental condition. Hence, the need for sequence information for developmental stage-specific promoters is evident.

Male reproductive development and ultimately, pollen formation in plants begins with meiosis. Meiosis consists of a complex set of processes involving homologous chromosome pairing, synapsis, chiasma formation and crossing over, chromosome segregation, and reductional division. In male meiosis of flowering plants, the product of meiosis is a callose-enclosed tetrad of haploid microspores, the precursors of pollen grains. Manipulation of gene expression using a genetic regulatory element such as the one described herein, whose role occurs early on in pollen development, has significant implications.

From the many meiotic mutants described in plants and other organisms, it is obvious that meiosis is an extremely complex event involving a large number of genes. While the dissection of meiosis by the isolation and characterization of mutants and the genes responsible has progressed in yeast and Drosophila, at present little is known of the molecular details of male meiosis and the very early development of microspores in flowering plants. Recently, however, several mutants have been described in *Arabidopsis thaliana* in which male gametophyte development is affected. Specifically, a T-DNA induced male-sterile mutant of *Arabidopsis thaliana* that is defective in meiosis and that produces tetrads that are abnormal in number and in size has been described by He et al., *Sex. Plant Reproduction* 9: 54-57 (1996). In this mutant, instead of the normal tetrad of four microspores being formed after meiosis, a "tetrad" consisting of from 5 to 8 microspores is formed. The microspores show a wide range of sizes and of DNA contents. Plants homozygous for the mutation were reported to be male sterile and not to produce filled siliques, although occasionally a few siliques containing a few seeds are produced by some homozygous mutant plants.

T-DNA insertional mutagenesis can be used to produce mutant plants. An *Agrobacterium tumefaciens* strain containing the cointegrate pGV3850: 1003 Ti plasmid with NOS and NPT plant markers and a bacterial NPT marker was used to create the Arabidopsis mutants described above. The disruption of the plant's normal genomic DNA by the insertion of a T-DNA gives rise to a non-functional gene and mutant phenotype. One of the resulting phenotypes is plants that are male-sterile, a desirable trait for the development of hybrid seed.

A common feature of Agrobacterium-mediated plant transformation is the appearance of T-DNA duplications and rearrangements in the plant genome. In other words, the insertion of the T-DNA vector is random and does not produce consistent and predictable results. To reproduce by mutagenesis the desired mutation in other plants would not be possible without undue experimentation. Information about a gene sequence involved in the meiotic events giving rise to viable pollen provides a new mechanism for manipulating those events and producing plants which are male sterile.

The current invention relates to a gene, MEI1, and its promoter that are involved in meiosis. Significantly, the gene seems only to function at male meiosis. A mutation in the MEI1 gene results in a plant that is male sterile, but female fertile. A mutant line of Arabidopsis, designated 6492, has a phenotype similar to plants carrying the MEI1 sequence, but is female sterile, indicating the involvement of a gene different from the MEI1 sequence described herein. The MEI1 gene is novel in that, even though there is a sequence of over 100 base pairs available beyond the 3' stop codon TAA, there is no evidence of a 3' end poly(A) tail of this gene. Because this gene has unique splicing signals, it may not be polyadenylated the same way that normal genes usually are.

Knowledge of the MEI1 gene sequence and its promoter provides new ways of producing transgenic plants possessing desired characteristics. The promoter for the MEI1 gene can be used to facilitate the expression of exogenous genes, for example, suicide genes, in a manner related directly to pollen development. The MEI1 gene itself can be used to facilitate the isolation of homologous genes in other plant species. An artificial gene coding for an antisense RNA can be introduced to prevent expression of the specific target gene to whose mRNA it is complementary, in this case, the MEI1 gene product crucial for meiosis.

SUMMARY OF THE INVENTION

The invention relates to an isolated DNA sequence comprising a nucleotide sequence capable of regulating the expression of a second DNA sequence when the DNAs are part of a recombinant DNA construct. The isolated molecule includes the nucleotide sequence of the promoter region derived from a meiosis specific gene, MEI1, of *Arabidopsis thaliana* having the sequence (SEQ ID NO.1) described in FIG. 1.

In another aspect, the invention relates to a vector comprising the isolated DNA molecule and further comprising a DNA sequence encoding a gene product. The DNA sequence is operably linked to the promoter.

In yet another aspect, the invention relates to the expression of a gene product which disrupts the function or formation of pollen. The DNA sequence to be expressed may be heterologous with respect to the promoter.

In still another aspect, the invention relates to a transgenic plant comprising the isolated DNA promoter sequence of the invention.

In yet another related aspect, the invention provides for the production of a transformed plant cell comprising the isolated DNA sequence and subsequently the growth of transgenic plants containing the characteristic phenotype bestowed by the expression of the gene inserted into the genome of the transformed cell.

In another aspect, the invention relates to a method of producing a male sterile plant, comprising the steps of: (1) providing a transformed plant that contains a recombinant DNA molecule that includes (a) a DNA sequence which inhibits pollen formation or function by altering meiosis; and (b) a MEI1 or homologous promoter from other plants that is operatively linked to the DNA sequence of the invention; and (2) growing the plant under conditions such that male sterility is achieved as a result of the recombinant DNA sequence.

In yet another aspect, the invention relates to a plant containing a recombinant DNA molecule which includes at least two elements: (1) a DNA sequence that inhibits pollen formation or function by altering meiosis; and (2) the MEI1 promoter. The MEI1 promoter is operatively linked to the DNA sequence that inhibits pollen formation or function by altering meiosis.

DETAILED DESCRIPTION OF THE INVENTION

In the description that follows certain conventions will be followed as regards the usage of terminology: The gene name appears in capital letters and is italicized (MEI1). Mutant genes are indicated by lower case letters and italics (mei1). Unitalicized capital letters denote the name of the protein gene product (MEI1).

The term "male sterility" in a plant refers to the absence of viable pollen. Determination of sterility can be accomplished by methods well known to those skilled in the art. The term "isolated DNA molecule", as it is commonly understood in the art, refers to a fragment of DNA that is isolated or cloned from the genomic DNA of an organism. Isolated DNA molecules may be chemically synthesized.

A gene is a region of DNA that controls a discrete hereditary characteristic, usually corresponding to a single protein or RNA. This definition includes the entire functional unit, encompassing coding DNA sequences, noncoding regulatory DNA sequences and introns. The term "gene product" includes RNAs and protein products for which a gene codes.

As used in this specification, a developmentally-specific promoter is any promoter that is active during a particular phase of plant development and is essentially inactive at other times. A gene and a promoter are to be considered to be operably linked if they are on the same strand of DNA, and are located relative to one another such that the promoter directs transcription of the gene. The presence of intervening DNA sequences does not preclude an operable relationship.

The term expression refers to the production of an observable phenotype by a gene, usually by the synthesis of a protein. Expression typically involves transcription of the gene into mRNA with the subsequent translation of the mRNA into protein. Transcription is under the control of a regulatory element, a promoter. The term cloning vector refers to a plasmid or phage that is used as a vehicle into which foreign DNA is inserted for the purposes of producing more genetic material or for transformation, that is, the introduction of foreign material into a plant or plant cell.

A gene that results in an altered plant phenotype is any gene whose expression leads to the plant exhibiting a trait or traits that would distinguish it from a plant of the same species not expressing the gene. Examples of such altered phenotypes include, but are not limited to, a different growth habit, premature or late flowering, increased or decreased yield, sterility, mortality, susceptibility to disease and insect infestation.

Isolation and Characterization of the MEI1 Gene and Promoter

Seeds from Arabidopsis plants heterozygous for mei1 were germinated on seed germination medium (SGM) containing 50 µg/ml kanamycin (Kan). Kanamycin resistant seedlings, which include both homozygous and heterozygous plants, were transferred to soil. Plants homozygous for the mei1 mutation are male sterile whereas, heterozygous plants are fertile. In seeds obtained from plants heterozygous for mei1, approximately one-fourth of the plants were Kan sensitive and wild-type and three-fourths were Kan resistant. Of the Kan resistant plants one-third were male sterile and thus homozygous for the mutation. These data indicated the existence of a single copy of the T-DNA in the genome.

DNA Blot Analysis Homozygous mutant plants were used for DNA blot analysis and for the isolation of plant DNA flanking the insert T-DNA. Genomic DNA from homozygous mutant plants was isolated by the method of Dellaporta et al. (*Plant Mol. Biol. Rep.* 1: 19–22 1989). The contents of this document and others containing methods used for this invention are incorporated by reference in their entirety. DNA was separated on 0.8% agarose gels and transferred to nylon membranes (Hybond-N, Amersham) in 10×SSC. DNA probes were labeled with [α-$^{32}$P]dCTP by random oligonucleotide priming. Pre-hybridization was carried out at 65° C. in a solution containing 6×SSC, 5×Denhardt's solution, 0.5% SDS, 200 µg/ml salmon sperm DNA and hybridization was done under the same conditions but with between 2×10$^5$ and 1×10$^6$cpm of $^{32}$P labeled probe. The membranes were washed at 65° C. twice in 2×SSC, once in 2×SSC plus 0.1% SDS and once in 0.1×SSC.

Both the T-DNA left border and the right border were used as probes for DNA blot analysis. The left border T-DNA probe covered the 2.9 kb EcoRI-HindIII region of pTiC58 HindIII fragment 10. The right border T-DNA probe covered the 1.1 kb HindIII-BamHI fragment 23 containing the 3' region of the NOS gene.

Cloning

The inverse polymerase chain reaction (PCR) technique was used to isolate plant DNA flanking the right border of the T-DNA. Genomic DNA from MEI-1 homozygous mutant plants was digested with PstI. Digestion with PstI was expected to produce a fragment larger than 5.9 kb that would consist of a part of the right T-DNA border and flanking plant DNA. The DNA was then phenol/chloroform extracted, ethanol precipitated in the presence of 0.1M sodium acetate and resuspended in water. DNA (2.0 µg) was self-ligated with 200U of T4 DNA ligase (New England Biolabs) in 500 µl reaction. Following ligation, the resulting DNA circles were used as templates for PCR. Two primers in opposite orientation to that for normal PCR within the T-DNA right border (RB) were used: primer a (TTA ATT GTT GCC GGG AAG CTA GAG)(SEQ ID NO.2); primer b (CAA CCT TCC GGC GTT CGT GG)(SEQ ID NO.3). The PCR reaction was carried out in a 30 µl reaction in the presence of 200 µM dNTP, 5 U AmpliTaq DNA polymerase, Stoffel Fragment (Perkin-Elmer) and 1 µM each of primers a and b. Amplification was carried out for 35 cycles (94° C. for 1 min; 72° C. for 2 min followed by a 10 min extension at 72° C. after the last cycle. An approximately 2 kb fragment consisting of a portion of the T-DNA right border with flanking plant DNA was isolated on a 1% agarose gel and purified by Gene Clean (Bio 101), digested with PstI and BamHI (New England Biolabs), and cloned into Bluescript plasmid (Stratagene). The resulting construct was designated pCH101. The 2 kb fragment was sequenced and found to contain 836 bp of T-DNA RB and 1107 bp of plant flanking DNA.

Screening a Genomic Library

The region of pCH101 between the BamHI and PstI sites which consists of a small region of the right border of T-DNA and plant flanking DNA was sequenced. Plasmid pCH101 was digested with PstI and HindIII (New England Biolabs), and an 889 bp plant genomic fragment flanking the T-DNA insert was produced. It was labeled with [α-$^{32}$P] dCTP by random oligonucleotide priming and used as a probe to screen a Columbia lambda genomic library. The library was constructed from a Sau3a partial digest of genomic DNA, ligated into the XhoI sites of the lambda GEM-11 vector (Promega). Plaques were transferred to nylon membranes (Amersham) in duplicate, denatured in 0.5 M NaOH/1.5 M NaCl, neutralized in 0.5 M Tris-HCl/1.5 M NaCl (pH 7.4), and washed in 2×SSC. The membranes were prehybridized, hybridized and washed as described for DNA blot analysis. Four positive clones were isolated. Clones I and II were digested with SacI. Each clone produced one insert and the inserts were cloned into Bluescript. By sequence analysis two of the clones, numbered 1 and 2 (later referred to as Fragments I and II), were found to be overlapping and together covered a length of about 16 kb which included the site where the T-DNA was inserted in the mutant plants. These two clones were used for sequencing and a total of about 10 kb of DNA, flanking the insertion site of T-DNA in the mutant, was sequenced.

A fragment obtained by digesting the cloned genomic DNA with ClaI and EcoRI was used to probe genomic DNA blots of wild-type and mutant plants. The results showed that in the mutant plants an expected band larger than 4 kb was found after HindIII digestion, but in the wild type DNA a band of about 2.5 kb was present. This difference in size of fragments between wild-type and mutant plants confirmed what was expected from the sequence data, that probe 1 was in close proximity to the T-DNA insertion.

Characterization of the MEI1 cDNA and Genomic Sequence

Screening cDNA Libraries

Two cDNA libraries were screened. The first was a cDNA library made from Landsberg erecta inflorescences with flower buds predominantly younger than stage 11 (Smyth et al., 1990). This library was constructed by using the Stratagene UniZAP kit to clone the cDNAs between EcoRI and XhoI sites (Weigel et al., 1992). CD4-7 was the second library. Equal amounts of mRNA isolated from tissue culture grown roots, 7 day old etiolated seedlings, rosettes from staged plants of different ages and 2 light regimes, and 40 aerial tissues (stems, flowers, siliques) from the same plants as the rosettes were used to make the library in lambda-PRL2, a derivative of lambdaZipLox (D'Alessio et al., 1992). Both libraries were obtained from Arabidopsis Biological Resource Center at Ohio State University. For screening the libraries, the hybridization procedure was the same as that described above for screening the genomic library.

A genomic fragment (2624 bp) between PstI and EcoRI (probe 3 in FIG. 2) was used to screen the cDNA library made to RNA from immature flower buds. Four cDNA clones were found. While they varied in size, sequence analysis showed that they were the same sequence (G1 in FIG. 2). The 3' end of this gene is approximately 600 bp away from the site of the T-DNA insertion in the mutant. Comparison of the base sequence of the cDNA with the genomic sequence indicated the presence of two introns and three exons coding for a peptide of 200 amino acids. No obvious overall similarities to any known protein were found. Complementation analysis described later indicated that G1 was not responsible for the mutation. Nucleotide sequence comparison of the genomic DNA clone with known sequences identified a partial sequence of 304 base pairs (G3 in FIG. 2) that had almost complete identity with an Arabidopsis transcribed sequence tag (accession number Z30915). This sequence, located about 6kb upstream from MEI1 and at the terminus of the genomic clone, has similarity to ACC oxidase (ethylene-forming enzyme) from a number of plants.

Figure 1:
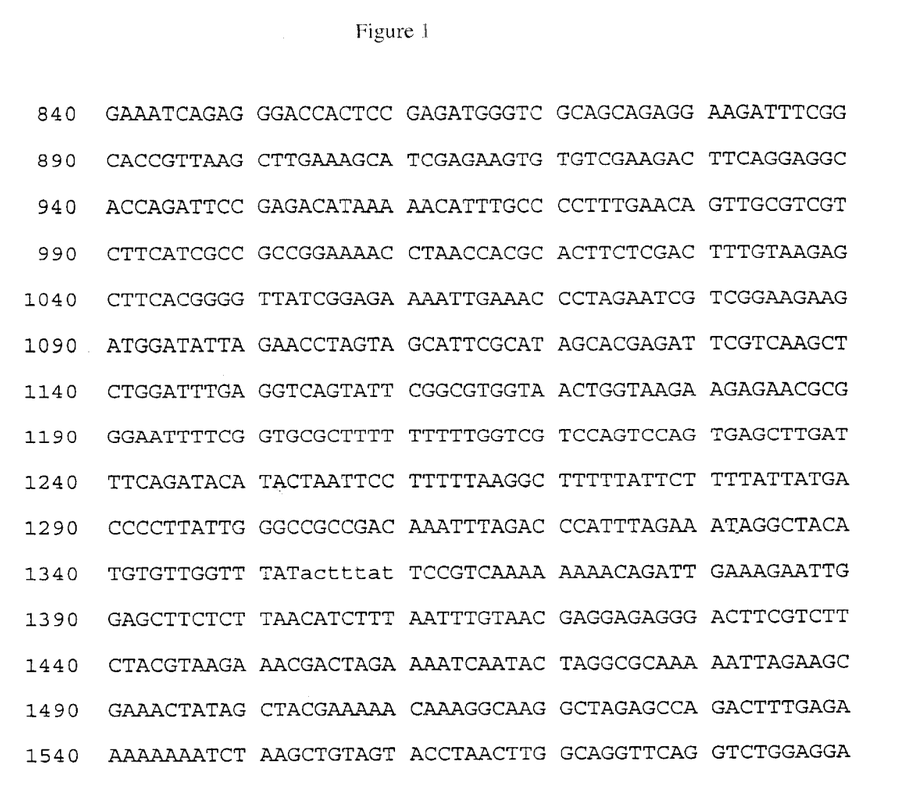
FIG. 1 lists a nucleotide sequence comprising the coding region of the genomic clone for MEI1, including the promoter sequence (SEQ ID NO.1). The sequence for the MEI1 promoter is included in the nucleotide sequence upstream of the ATG start site of translation at position 1–3.

The two cDNA libraries were then screened using a smaller DNA fragment (1739 bp in length between HindIII and EcoRI (probe 4 in FIG. 2) that included the site of T-DNA insertion but excluding the cDNA1 sequence. This screen was not successful. Because of the possibility that the MEI1 mRNA was of low abundance, a polymerase chain reaction (PCR) approach was used to screen the two cDNA libraries. Two primers were designed from the T-DNA insertion region: 5'CGGTCTCGAGATCTTCCTCTGCT-GCGACCC 3' (SEQ ID NO.4) and 5' TTGGGATCCG-CAGCCAAGACATTTTTCACAA 3' (SEQ ID NO.5). About 5×10$^6$ clones were screened without success. The same primers were then used for reverse transcriptase PCR using RNA isolated from immature wild-type flowers; a cDNA fragment of about 400 bp was obtained. Nucleotide sequence comparison between the cDNA and the genomic sequence in this region showed the presence of a gene (G2 in FIG. 2) in the genomic DNA which contained at least two introns. The nucleotide sequence of the genomic DNA that includes G2 is presented in FIG. 1. Since there is a stop codon at position 755-757 the cDNA fragment probably represents the 3' end of the mRNA. Accordingly, another pair of primers, 5' GAAGATCTGGTAGATGAGAAGGT-CAAGATC 3'(SEQ ID NO.6) AND 5' CGGAATTCT-GATCGCAATCTTTGAAC 3' (SEQ ID NO.7) was used to recover the 5' end of the gene. This resulted in a fragment that allowed us to extend the sequence of the 5' end of the mRNA by 34 nucleotides. There is a stop codon in the 5' region of this sequence and a potential TATA box upstream of the sequence in the genomic DNA; indicating that the entire coding region of the gene has been recovered. The sequence in FIG. 1 is numbered with the A in the translation start codon as +1.

Sequencing

EcoRI digestion of two of the genomic clones isolated by screening of the genomic library generated smaller restriction fragments, which were cloned into Bluescript plasmid. Sequencing was performed by the dideoxynucleotide chain termination method (Sanger et al., 1977) using Sequenase version 2.0 (U.S. Biochemical/Amersham). T3 and -20 primers from the plasmid sequence and gene-specific primers were used to generate overlapping sequence information. The junction region extending across the genomic fragment flanking the T-DNA and the right border of the T-DNA was amplified by reverse PCR and sequenced. Sequence analysis and comparison were accomplished by using the BESTFIT program and the BLAST program in the GCG package (Program Manual for the Wisconsin package, version 9.1 UNIX, 1997, Genetics Computer Group, Madison, Wis.).

The gene codes for a polypeptide, 89 amino acids in length. Comparative sequence analysis did not identify any protein in the data bases that showed significant similarity to the protein product of MEI-1, although the protein exhibits 42% similarity and 20% identity over almost its entire sequence with the human acrosin-trypsin inhibitor (HUSI-II), a member of the Kazal-type serine proteinase inhibitors. The two differ, however, in that, while the basic structure of Kazal inhibitors consists of 6 cysteine residues spaced at defined intervals, the MEI-1 protein contains only 3 of the cysteine residues.

Intron/exon Junctions in the MEI1 Gene

The comparison between the nucleotide sequences of the cDNA and genomic clones indicated the presence of two introns in MEI-1. These are indicated in FIG. 1 by . . . For neither intron do the 5' and 3' splice sites seem to comply with the :GU . . . AG: rule.

GU and AG dinucleotides which flank plant introns are highly conserved. A recent analysis of 998 Arabidopsis intron sequences in the EMBL database showed that even though most introns adhere to the GU . . . AG: rule, there is a 1% exception that have GC at their 5' ends. Both introns are strongly enriched in A+T nucleotides (68% and 73% respectively), which is the essential feature for their processing and required for efficient splicing. In the yeast, *Saccharomyces cerevisiae*, an additional essential signal is the highly conserved UACUAAC (SEQ ID NO.8) branch-point sequence (the branchpoint nucleotide is underlined), located in most instances 10–50 nucleotides upstream of the 3' splice site. In vertebrates, a loosely conserved consensus branchpoint sequence, UNCURAC or CURAC, has been derived from direct determination of branch sites utilized during splicing of different introns. The branchpoint sequence in vertebrates is usually located 18–40 nucleotides upstream of the 3' splice site. Plant introns were thought to contain neither conserved branchpoint sequences nor distinct 3' proximal polypyrimidine tracts characteristic of yeast and vertebrate introns, respectively. But recent studies showed that the branchpoint sequences (YUNAN) for intron lariat formation located 21–60 nucleotides upstream of the 3' splice site are required for the efficient splicing of at least some plant introns in addition to the important role played by AU sequences. The putative consensus branchpoint sequences (YUNAN) for intron lariat formation are also positioned upstream of the 3' splice site in both introns. CTGAC (SEQ ID NO.9), CTAAA (SEQ ID NO.10), CTAAT (SEQ ID NO.11) are 12, 33, 41 nucleotides respectively away from the 3' splice site in the first intron; CTCAT (SEQ ID NO.12), TTAAG (SEQ ID NO.13), TTTAT (SEQ ID NO.14), TTGAT (SEQ ID NO.15) are 6, 33, 37, 41 nucleotides respectively away from the 3' splice site of the second intron. They may play a role in their splicing.

There are 7 possible sites where splicing could occur for the first intron and 5 for the second intron which would result in the same coding sequence in the mRNA. None of these possible sites, however, conforms to the :GU . . . AG: rule. The sequences common to these two introns indicate that the introns have CU at their 5' ends and AC at their 3' ends instead of GU and AG.

Complementation Aanalysis

Figure 2:
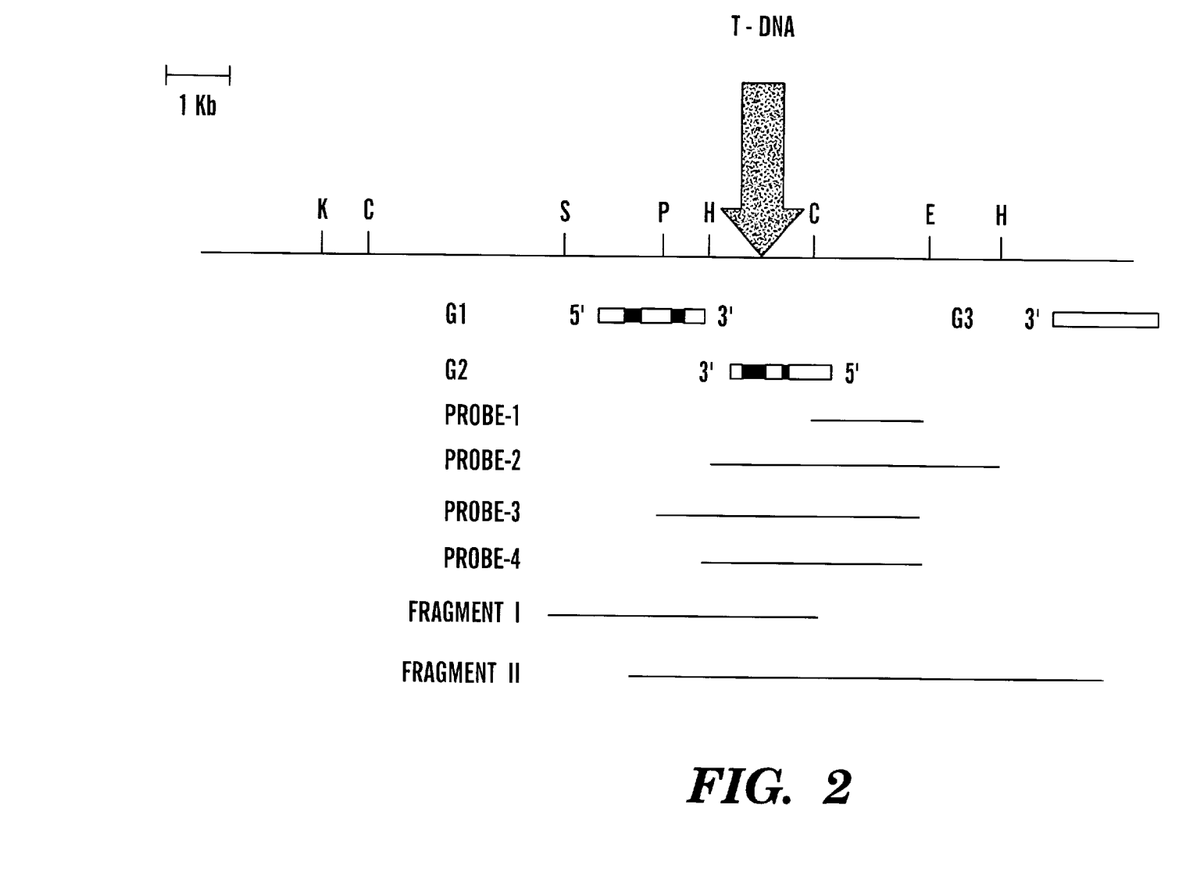
FIG. 2 represents a partial restriction map showing the location of the T-DNA insertion site, cDNAs, DNA probes used and DNA fragments used for complementation analysis.

Two wild-type genomic DNA fragments were used to complement the mutation. The first genomic DNA fragment, 2601 bp in length contained a gene, G1 (FIG. 2). The 3'-end of this fragment is approximately 600 bp away from the T-DNA insertion site in the mutant. It was generated by digesting the genomic clone I with ClaI and SpeI and then cloned into Bluescript and designated p3.12. The plasmid, pCPL951, was constructed by cloning the 2601 bp fragment from p3.12 into the plant transformation vector pCIT20 (Ma et al. 1992) between the SacI and ClaI sites at the multicloning site. The second genomic DNA fragment, 7982 bp in size, fragment II (FIG. 2) contained the entire genomic sequence of MEI1. The two fragments overlapped but fragment I did not contain the 5' coding region of the MEI1 gene. Fragment II contained the entire gene, a transcript of which corresponds to G2 (FIG. 2). This gene is disrupted by T-DNA in the mutant. Fragment II was cloned into pCIT20 between two SacI sites in the multicloning site, to form pCPL961. pCPL951 and pCPL961 were mobilized into Agrobacterium EHA 101 and EHA105 and transformants were generated from hypocotyl sections by the method of Lin et al. (1994). Since the hygromycin resistance (hygr) gene is the selection marker in pCIT20, 20 μg/ml hygromycin B (Sigma) was used for selection of transformants.

Confirmation by Complementation, that the Isolated Sequence Represents the MEI1 Gene Two wild-type DNA fragments, I and II, (2.6 Kb and 8.0 Kb in size respectively) spanning the T-DNA insertion site were introduced into the plant transformation vector pCIT20, which confers resistance to hygromycin. The resulting plasmids, pCPL951 and pCPL961, were transformed into Arabidopsis plants containing the mei1 mutation.

Hypocotyls from homozygous and heterozygous plants and one-week old seedlings were used as explants for transformation. While it is preferable to use hypocotyls from only homozygous mei1 plants, homozygous mei1 plants were not distinguishable from heterozygous plants at this stage. Selection was for both kanamycin and hygromycin resistance. The seeds from the resulting transformants were first germinated on SGM containing kanamycin for a week and kanamycin resistant seedlings were then grown on hygromycin containing medium. Seeds from individual plants of the T1, T2, or T3 generations were selected on kanamycin medium to identify plants homozygous for kanamycin resistance. Such kanamycin resistant plants were also selected for hygromycin resistance. Unless the mutation was complemented one would not expect to obtain plants homozygous for kanamycin resistance. A wild-type, that is, male fertile phenotype was observed in ten independent transformants with the 8 kb genomic fragment, but none from the 2.6kb fragment. These included 4 that were homozygous for both kanamycin and hygromycin resistance, and 6 that were homozygous for kanamycin resistance but heterozygous for hygomycin resistance. The 8.0 kb (7982 bp) genomic fragment thus complemented the mutation. That the complemented plant had the initial T-DNA insert was confirmed by DNA blot analysis using DNA from a plant homozygous for both kanamycin and hygromycin resistance.

The 2.6 kb fragment which did not complement the mei1 mutation contained the coding region of gene 1, approximately 500 bp of 5' flanking sequence of the promoter region, and about 600 bp of the 3' end of the MEI1 gene. The failure of this fragment to complement the mei1 mutation indicates that the G1 gene has some other function.

Characterization of the T-DNA Right Border and Flanking Genomic DNA

The last 366 bp of the T-DNA right border extending from base number 16,544 to 16,909 and another 25 bp fragment between 16,462 to 16,486 bp, were found to be missing in the mutant genome. Attempts to recover, by PCR analysis, the sequence at the junction of the left T-DNA border and the flanking plant genomic sequence were not successful. Because of rearrangements and deletions, sequencing of these DNAs is not straightforward or routine.

With the identification of the MEI1 gene and its promoter, it is now possible, using standard techniques such as that used in the complementation analysis described above, to introduce into plants a nucleotide construct, or vector, containing the promoter and one or more genes endogenous or exogenous to the plant. In this way the expression of genes in pollen can be regulated. The methods discussed here can also be used to interfere with the normal development of pollen or to provide pollen with new characteristics.

Techniques well known in the art can be used to introduce the pollen-specific MEI1 promoter and exogenous or endogenous genes into plants for the purpose of preventing pollen development. Suicide genes which would result in abortion of pollen development and hence male sterility are one example. Such genes include those that produce a toxic compound or a hydrolytic enzyme such as DNase. Another example is artificial genes such as the antisense of MEI1 which can be generated by methods well know to a person of ordinary skill in the art. An artificial gene coding for an antisense RNA can be introduced to prevent expression of the specific target gene to whose mRNA it is complementary, in this case, a gene product crucial for meiosis.

Transformation Methods

Transformation methods include a number of different well known methods for direct DNA delivery. For monocots, such as corn, delivery of DNA to the treated cells by particle bombardment is a particularly effective method, but other methods such as electroporation can also be used. For dicots, Agrobacterium delivery to explants is most commonly used. Other methods include Agrobacterium cocultivation of protoplasts; electroporation; PEG uptake or other direct DNA delivery into protoplasts and the like.

Cells of a plant are transformed with the foreign DNA sequence of this invention in a conventional manner. If the plant to be transformed is susceptible to Agrobacterium infections, it is preferred to use a vector containing the foreign DNA sequence which is a disarmed Ti plasmid. The transformation can be carried out using procedures described, for example, in EP 0 116 718 and EP 0 270 822. Preferred Ti plasmid vectors contain the foreign DNA sequence between the border sequences, or at least located upstream of the right border sequence. Other types of vectors can be used for transforming the plant cell, using procedures such as direct gene transfer as described in EP 0 237 356 and EP 0 275 069; in vitro protoplast transformation as described in U.S. Pat. No. 4,684,611; plant virus-mediated transformation as described in EP 0 067 553 and U.S. Pat. No. 4,407,956; and liposome-mediated transformation as described in U.S. Pat. No. 4,536,475.

If the plant to be transformed is corn, recently developed transformation methods are suitable such as the methods described by Fromm et al., 1990, and Gordon-Kamm et al. 1990.

If the plant to be transformed is wheat, a method analogous to those described above for corn or rice can be used. Preferably for the transformation of a monocotyledonous plant, particularly a cereal such as rice, corn or wheat a method of direct DNA transfer, such as a method of biolistic transformation or electroporation, is used.

A Method for Transformation by Particle Bombardment

A method for transformation by particle bombardment is given in U.S. Pat. No. 5,689,049, including a protocol for corn transformation to recover stable transgenic plants.

The present invention has been described with regard to preferred embodiments. However, it will be obvious to persons skilled in the art that a number of variations and modifications can be made without departing from the scope of the invention as described in the following claims.

All patents, publications, or other references that are listed herein are hereby incorporated by reference.

What is claimed is:

1. An isolated nucleic acid comprising a nucleotide sequence isolated from the MEI1 gene of *Arabidopsis thaliana*, said nucleotide sequence having promoter activity.

2. The isolated nucleic acid of claim 1, wherein said nucleotide sequence comprises SEQ ID NO: 16.

3. A vector comprising the isolated nucleic acid of claim 1.

4. The vector of claim 3, further comprising a nucleotide sequence encoding a gene product, said nucleotide sequence operably linked to said promoter.

5. The vector of claim 4, wherein said gene product disrupts the function or formation of pollen.

6. The vector of claim 4, wherein said nucleotide sequence is heterologous with respect to said promoter.

7. A transgenic plant containing the vector of claim 3.

8. A transformed plant cell containing the vector of claim 3.

9. A plant generated from the plant cell of claim 9.

10. An isolated nucleic acid comprising a meiosis-specific promoter of *Arabidopsis thaliana*, said promoter comprising the nucleotide sequence of SEQ ID NO: 16.

11. An isolated promoter of *Arabidopsis thaliana* isolated from the nucleotide sequence of SEQ ID NO.: 1.

12. An isolated nucleic acid comprising the sequence of SEQ ID NO.: 16.

13. A vector comprising the isolated nucleic acid of claim 12.

14. The vector of claim 13 further comprising a nucleotide sequence encoding a gene product, said nucleotide sequence operably linked to said promoter.

15. The vector of claim 14, wherein said nucleotide sequence is heterologous with respect to said promoter.

* * * * *

UNITED STATES PATENT AND TRADEMARK OFFICE
CERTIFICATE OF CORRECTION

PATENT NO.     : 6,476,297 B1                                              Page 1 of 1
DATED          : November 5, 2002
INVENTOR(S)    : Mascarenhas et al.

It is certified that error appears in the above-identified patent and that said Letters Patent is hereby corrected as shown below:

<u>Title page,</u>
Item [75], Inventor, delete "Mascarehas" and insert -- Mascarenhas --

Signed and Sealed this

Fourth Day of March, 2003

JAMES E. ROGAN
*Director of the United States Patent and Trademark Office*